United States Patent [19]

Bunke

[11] 4,132,502
[45] Jan. 2, 1979

[54] SPATULA FOR MIXING PLASTIC SUBSTANCES

[75] Inventor: Klaus Bunke, Leverkusen, Germany

[73] Assignee: Bayer Aktiengesellschaft, Leverkusen, Germany

[21] Appl. No.: 798,743

[22] Filed: May 19, 1977

[30] Foreign Application Priority Data

Jun. 10, 1976 [DE] Fed. Rep. of Germany ....... 2625920

[51] Int. Cl.$^2$ .......................... B01L 3/18; A47J 43/28
[52] U.S. Cl. ...................................... 416/70 R; 7/113; 7/158
[58] Field of Search .................. 416/70, 71, 227, 228, 416/146 R; 366/129, 130, 342, 343; 7/1 A, 1 B, 14.1 R, 14

[56] References Cited

U.S. PATENT DOCUMENTS

| | | | |
|---|---|---|---|
| D. 47,443 | 6/1915 | Villemain | 7/1 A |
| 717,998 | 1/1903 | Huebner | 7/1 A |
| 849,098 | 4/1907 | Aufrichtig | 7/1 B |
| 972,777 | 10/1910 | Richardson | 7/14 |
| 1,288,617 | 12/1918 | Kupiszewski | 7/1 A |
| 1,434,744 | 11/1922 | Hibbler | 7/1 A |
| 1,732,714 | 10/1929 | Copes | 416/70 |
| 2,524,475 | 10/1950 | Renz | 416/71 |
| 2,670,939 | 3/1954 | Harp | 416/71 |
| 3,411,723 | 11/1968 | Kohn | 416/71 |

*Primary Examiner*—Everette A. Powell, Jr.
*Attorney, Agent, or Firm*—Sprung, Felfe, Horn, Lynch & Kramer

[57] ABSTRACT

A spatula is formed as a combination implement. Several mixing implements which are suitable for substances of varying consistency are placed on one and the same handle unit. There is preferably a knife-blade-type mixing implement at one end of the handle and a pronged, fork-type mixing implement at the other end.

6 Claims, 5 Drawing Figures

SPATULA FOR MIXING PLASTIC SUBSTANCES

The invention relates to a spatula for mixing plastic substances, in particular for dental purposes.

In a spatula of this type which is widely used in the dental sphere, the knife-blade-type mixing implement is made of metal; as opposed to a knife blade, however, it is symmetrical about the longitudinal axis. Like a knife blade, it is inserted in a haft-type handle unit which is made of non-metallic material. Spatulas of this type are suitable for mixing easily flowing moulding substances. However, silicone moulding substances of tough plastic consistency among other things have been used recently, these substances having to be mixed with a hardener-fluid or hardener-paste before an impression is produced, and then taking on a condition which resembles a hard rubber. The spatulas used in the past are, for many reasons, unsuitable for mixing the hardener-fluid or hardener-paste; there are difficulties in mixing the relatively small quantity of hardener sufficiently quickly and above all sufficiently evenly, as required for producing an impression which has an approximately even solidity throughout.

The object of the invention is to produce a spatula which is suitable not only for mixing easily flowing moulding substances, but also for mixing tough plastic substances, and, without difficulties, allows embodiments which may be simply and cheaply produced, which correspond to the predominating requirements for simple sterilization in the medical sphere and which may also be compactly stored and easily packed and despatched.

According to the invention, there is provided a spatula for mixing plastic substances, comprising a handle unit having arranged thereon a plurality of mixing implements, including a knife-blade-type mixing implement.

The knife-blade-type mixing implement is preferably arranged at one end of the handle unit and a mixing implement comprising a plurality of spikes at the other end.

Whereas the knife-blade-type mixing implement is suitable for mixing easily flowing mould substances, as in the past, the implement having spikes laying alongside each other in the manner of a fork at the other end of the handle unit enables hardener-fluids or hardener pastes to be mixed in the mentioned tough plastic silicone mould substances rapidly and with even distribution.

The various implements are appropriately placed at the ends of the handle unit in an axial direction. In this manner, the dimensions of the spatula according to the invention may be kept small, transversely to the main axis.

In a preferred embodiment, the implement having spikes in the manner of fork prongs forms an essentially shorter section in the longitudinal direction than the knife-blade-type implement, so the handle unit is displaced from the linear centre towards the spiked appliance. In this manner, slightly higher forces may be exercised by the mixing forks than with the knife-blade-type implement.

For the sake of economy in production and of problem-free sterilization, the handle unit and the various implements placed at its ends are comprised of one piece. This is particularly valid if the assembly is produced from a plastics material, in particular polystyrene. It then not only allows for any mechanical requirements, but the spatulas formed in this way are also completely resistant to corrosion and, in addition, look nice, since white, or white-translucent plastic substances may be used for production without further problems and appearance of these plastics being suitable for the usual image in the medical sphere. Insofar as there is an increased risk of fracture during inexpert handling, when using plastics for the knife-blade-type appliance, this is counteracted by the appliance being strengthened along its longitudinal axis, preferably in such a way that its cross-section forms a flat lozenge which is flattened towards the free end of the implement.

The fact that the handle unit is of the same thickness as the implement having the spikes in the manner of fork prongs and if formed flat, promotes material saving as well as easy storage and packing; handling is simplified by the handle unit having a finger hollow on at least one of its faces. The finger hollow may also easily hold a written character which is integrated in the injection moulding dye or to be impressed, for example for advertising purposes.

The possibility of exercising large forces on small surfaces is also promoted by the fork-prong-type spikes being formed of different lengths, by their points lying in a line which is inclined to the longitudinal axis of the spatula; if necessary it is easier to operate in such a way that the spikes do not all need to function simultaneously.

In the drawings which show an embodiment of a spatula according to the invention, FIG. 1 shows a plan of the spatula, FIG. 2 shows a longitudinal section through the spatula, FIG. 3 shows a section along line 3—3 in FIG. 1

Figure 1:
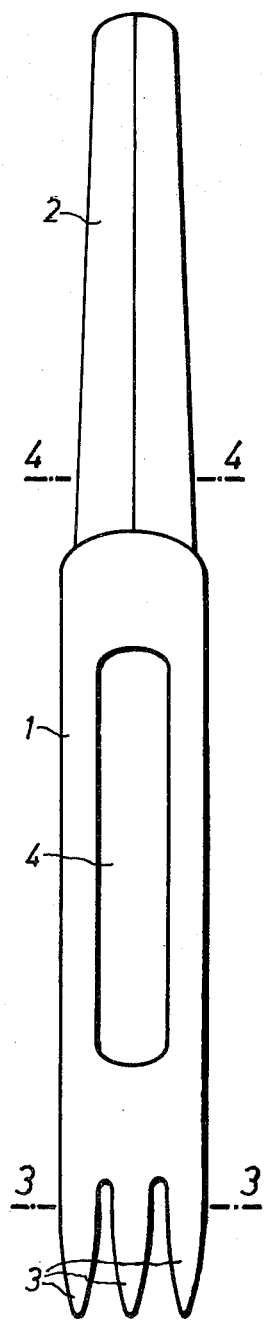
Figure 2:
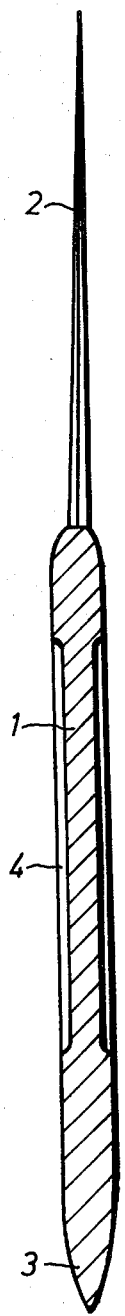
Figure 4:
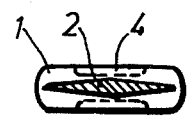
FIG. 4 shows a section along line 4—4 in FIG. 1.
Figure 3:
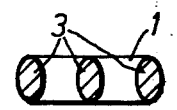

In the embodiment shown, a handle unit 1 having a knife-blade-type mixing implement 2 as shown in the plane of FIG. 1 and an additional implement, arranged at its other end, having adjacent spikes 3, is produced from one piece of plastics. The spikes 3 are pointed and have the cross-section shown in FIG. 3; they run up and down like blades and are higher than wide, so that they are particularly capable or resisting the forces which occur when they are trodden on. As a result of this configuration of the spike cross-sections, the intervals between the spikes decrease towards the middle thus benefiting the mixing effect when substances are crushed between the spikes. The knife-blade-type mixing implement 2 has the lozenge shape cross-section shown in FIG. 4. Finger hollows 4 are arranged on both faces of the handle unit 1 shown in the Example.

Figure 5:
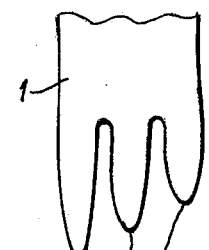
FIG. 5 shows a partial plan of another embodiment of the spatual.

As shown in FIG. 5, the fork spikes 3' have different lengths and their points lie in a line which is inclined to the longitudinal axis of the spatula.

I claim:

1. Spatula for mixing plastic substances such as for dental purposes or the like, comprising: an elongated knife-blade portion symmetrical about its longitudinal axis and strengthened along its entire longitudinal length such that the cross-section forms a flat lozenge which becomes flatter and narrower towards one end thereof; an elongated handle unit connected at one end to the other end of the knike blade portion wherein the handle unit is substantially flat and has a given width;

and an implement having fork-like spikes which lie adjacent to each other and disposed at the other end of the handle unit and having substantially the same width, wherein the implement has an essentially shorter section in the longitudinal direction than the knife-blade portion, so that the handle unit is displaced from the linear center of the spatula toward the implement; wherein the knife blade portion and the implement are disposed on either side of the handle unit to define a substantially flat elongated spatula.

2. Spatula according to claim 1, wherein the handle unit, the knife blade portion and implement are integral members.

3. Spatula according to claim 2, wherein the integral member is one of wood, metal or plastic.

4. Spatula according to claim 1, wherein the handle unit has a finger hollow on at least one of its main faces.

5. Spatula according to claim 4, wherein the finger hollow has indicia thereon.

6. Spatula according to claim 1, wherein the spikes vary in length and that their points lie on a line which is inclined to the longitudinal axis of the spatula.

* * * * *